United States Patent [19]
Sebti et al.

[11] Patent Number: 5,856,310
[45] Date of Patent: Jan. 5, 1999

[54] INHIBITION OF FARNESYLTRANSFERASE

[75] Inventors: Said Sebti; Andrew Hamilton; Churl Min Seong, all of Pittsburgh, Pa.

[73] Assignee: University of Pittsburgh, Pittsburgh, Pa.

[21] Appl. No.: 464,203

[22] Filed: Jun. 5, 1995

Related U.S. Application Data

[62] Division of Ser. No. 62,287, May 18, 1993.

[51] Int. Cl.$^6$ ...................................................... A61K 38/00
[52] U.S. Cl. .................................. 514/19; 514/18; 514/7; 530/331
[58] Field of Search .................................. 514/18, 19, 7; 530/331

[56] References Cited

U.S. PATENT DOCUMENTS

| | | | |
|---|---|---|---|
| 5,043,268 | 8/1991 | Stock | 435/15 |
| 5,141,851 | 8/1992 | Brown | 514/18 |
| 5,238,922 | 8/1993 | Graham et al. | 514/18 |

FOREIGN PATENT DOCUMENTS

| | | |
|---|---|---|
| 2072033 | 6/1992 | Canada . |
| 0203587 | 12/1986 | European Pat. Off. . |
| 0456180 | 11/1991 | European Pat. Off. . |
| 0461869 | 12/1991 | European Pat. Off. . |
| 0512865 | 11/1992 | European Pat. Off. . |
| 0520823 | 12/1992 | European Pat. Off. . |
| 0523873 | 1/1993 | European Pat. Off. . |
| 0528486 | 2/1993 | European Pat. Off. . |
| 0534546 | 3/1993 | European Pat. Off. . |
| 0535730 | 4/1993 | European Pat. Off. . |
| 351085A | 10/1985 | Germany . |
| WO9116340 | 10/1991 | WIPO . |
| WO9218465 | 10/1992 | WIPO . |

OTHER PUBLICATIONS

Hancock et al, "A polybasic Domain or Palmitoylation is Required in Addition to the CAAX Motif to Localize p 21$^{ras}$ to the Plasma Membrane", Cell, vol. 63, Oct. 5, 1990 pp. 133–139.

Reiss et al, "Inhibition of Purified p21$^{ras}$ Farnesyl:Protein Transferase by Cys–AAX Tetrapeptides", Cell, vol. 62, Jul. 13, 1990, pp. 81–88.

Willumsen et al, "The p21 ras C–terminus is required for transformation and membrane association," Nature, vol. 310, Aug. 16, 1984, pp. 583–586.

Harde, Bioorg Med Chem Lett 4, 273, 1994.

Farrington, Arch Bioch Biophys 307, 165, 1993.

*Primary Examiner*—Cecilia J. Tsang
*Assistant Examiner*—David Lukton
*Attorney, Agent, or Firm*—Cushman Darby & Cushman IP Group of Pillsbury Madison & Sutro

[57] ABSTRACT

Peptidomimetics of the formula C-AMBA-X where C is cysteine, X is, for example, methionine or phenylalanine and AMBA is a hydrophobic spacer, notably 3-aminomethylbenzoic acid. These compounds are effective inhibitors of p21ras farnesyltransferase. Other modifications including alternative spacers for AMBA, and replacement of the $A_1A_2X$ component of known $CA_1A_2X$ tetrapeptides by a non-peptide aryl or heterocyclic component are also disclosed as are various phosphorylated and arylated derivatives of peptides and peptidomimetics. Pro-drugs made by functionalizing terminal amino and carboxylic acid groups of peptides and peptidomimetics are also disclosed. Such functionalized derivatives demonstrate increased cell uptake. Other structural modifications are also referred to.

5 Claims, 6 Drawing Sheets

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label= X
            / note= "ALIPHATIC AMINO ACID"

( i x ) FEATURE:
        ( A ) NAME/KEY: Modified-site
        ( B ) LOCATION: 3
        ( D ) OTHER INFORMATION: /label= X
            / note= "ALIPHATIC AMINO ACID"

( x i ) SEQUENCE DESCRIPTION: SEQ ID NO:1:

Cys  Xaa  Xaa  Xaa
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Cys  Val  Ile  Met
    1

( 2 ) INFORMATION FOR SEQ ID NO:3:

( i ) SEQUENCE CHARACTERISTICS:
   ( A ) LENGTH: 6 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:3:

Thr Lys Cys Val Ile Met
 1                5

( 2 ) INFORMATION FOR SEQ ID NO:4:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:4:

Lys Lys Ser Lys Thr Lys Cys Val Ile Met
 1                5                   10

( 2 ) INFORMATION FOR SEQ ID NO:5:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:5:

Val Cys Ile Met
 1

( 2 ) INFORMATION FOR SEQ ID NO:6:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:6:

Cys Ile Ile Met
 1

( 2 ) INFORMATION FOR SEQ ID NO:7:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:7:

Cys Val Val Met
 1

INHIBITION OF FARNESYLTRANSFERASE

This is a continuation division of application Ser. No. 08/062,287, filed May 18, 1993.

INTRODUCTION

The present invention relates to novel peptidomimetics and other compounds which are useful as inhibitors of p21ras farnesyltransferase. Farnesylation is required for the cancer causing activity of the oncogene product p21ras. Hence there is considerable interest in inhibiting farnesylation.

The invention was supported by grants from the American Cancer Society and the National Cancer Institute (NIH).

BACKGROUND OF THE INVENTION

Ras oncogenes are the most frequently identified activated oncogenes in human tumors (1–3). It is known that the ras oncogenes encode 21,000 dalton G-proteins (p21ras) which play an essential role in growth factor signal transduction, proliferation and malignant transformation (1–7). Association of p21ras with the plasma membrane is required for its transforming activity (8,9). Post-translational events leading to membrane association of p21ras have previously been disclosed (10–14). The p21ras proteins are first made as pro-p21ras in the cytosol where they are modified on cysteine 186 of their carboxyl terminal sequence $CA_1A_2X$ (C=cysteine, $A_1$ and $A_2$=isoleucine, leucine or valine and X=methionine or serine) by the cholesterol biosynthesis intermediate farnesyl pyrophosphate (FPP). This farnesylation reaction is then followed by peptidase removal of the $A_1A_2X$ tripeptide and carboxymethylation of the remaining cysteine. The processed p21ras proteins associate with the inner surface of the plasma membrane and are further modified on cysteines 181–184 by another lipid, palmitic acid (10–14).

p21Ras farnesyltransferase, the enzyme responsible for catalyzing the transfer of farnesyl, a 15-carbon isoprenoid, from FPP to the cysteine of the $CA_1A_2X$ carboxyl terminus of p21ras, has been purified to homogeneity from rat brain (15,16). The enzyme is a heterodimer composed of α and β subunits of molecular weights 49 and 46 kDa, respectively (17). The β subunit has been shown (17) to bind p21ras and the α subunit is believed to bind FPP. Because p21ras farnesylation and subsequent membrane association are required for p21ras transforming activity, it has been proposed that p21ras farnesyltransferase would be a useful anticancer therapy target. Accordingly, an intensive search for inhibitors of the enzyme is underway (18–24). Potential inhibitor candidates are $CA_1A_2X$ tetrapeptides which have been shown to be farnesylated by p21ras farnesyltransferase and appear to be potent inhibitors of this enzyme in vitro (15,18,21–24). Competition studies have demonstrated that $CA_1A_2X$ peptides with the greatest inhibitory activity are those where $A_1$ and $A_2$ are hydrophobic peptides with charged or hydrophilic residues in the central positions demonstrating very little inhibitory activity (18,21,23).

The research efforts directed towards farnesyltransferase and the inhibition of its activity are further illustrated by the following patents or published patent applications:

U.S. Pat. No. 5,141,851

WO 91/16340

WO 92/18465

EPA 0456180 A1

EPA 0461869 A2

EPA 0512865 A2

EPA 0520823 A2

EPA 0523873 A1

Of the above disclosures, EPA 0520823 A2 discloses compounds which are useful in the inhibition of farnesyl-protein transferase and the farnesylation of the oncogene protein ras. The compounds of EPA 0520823 A2 are illustrated by the formula:

$$Cys\text{-}Xaa^1\text{-}Xaa^2\text{-}Xaa^3$$

or pharmaceutically acceptable salts thereof, wherein Cys is a cysteine amino acid;

$Xaa^1$ is an amino acid in natural L-isomer form;

$dXaa^2$ is an amino acid in unnatural D-isomer form; and $Xaa^3$ is an amino acid in natural L-isomer form.

The preferred compounds are said to be CV(Dl)S and CV(Df)M, the amino acids being identified by conventional 3 letter and single letter abbreviations as follows:

| Cysteine | Cys | C |
| Glycine | Gly | G |
| Isoleucine | Ile | I |
| Leucine | Leu | L |
| Lysine | Lys | K |
| Methionine | Met | M |
| Phenylalanine | Phe | F |
| Serine | Ser | S |
| Threonine | Thr | T |
| Valine | Val | V |

EPA 0523873 A1 discloses a modification of the compounds of EPA 0520823 A2 wherein $Xaa^3$ is phenylalanine or p-fluorophenylalanine.

EPA 0461869 describes compounds which inhibit farnesylation of Ras protein of the formula:(SEQ ID NO: 1)

$$Cys\text{-}Aaa^1\text{-}Aaa^2\text{-}Xaa$$

where $Aaa^1$ and $Aaa^2$ are aliphatic amino acids and Xaa is an amino acid. The aliphatic amino acids which are disclosed are Ala, Val, Leu and Ile. Preferred compounds are those where $Aaa^1$ is Val, $Aaa^2$ is Leu, Ile or Val and Xaa is Ser or Met. Preferred specific compounds are:

Cys-Val-Leu-Ser

Cys-Val-Ile-Met

Cys-Val-Val-Met

U.S. Pat. Nos. 5,141,851 and WO 91/16340 disclose the purified farnesyl protein transferase and certain peptide inhibitors therefor, including, for example, CVIM, TKCVIM and KKSKTKCVIM (SEQ ID NO:2 through SEQ ID NO:4), WO 92/18465 discloses certain farnesyl compounds which inhibit the enzymatic methylation of proteins including ras proteins.

EPA 0456180 A1 is directed to a farnesylprotein transferase assay which can be used to identify substances that block farnesylation of ras oncogene gene products while EPA 0512865 A2 discloses certain cyclic compounds that are useful for lowering cholesterol and inhibiting farnesyl-protein transferase.

As will be evident from the foregoing, there is a great deal of research effort directed towards the development of inhibitors of farnesyltransferase. However, there still remains a need for improvements in this critically important area.

SUMMARY OF THE INVENTION

An important embodiment of the present invention is based on the finding that a novel group of peptidomimetics as represented by Formula (I) have a high inhibitory potency against human tumor p21ras farnesyltransferase:

$$\text{C-AMBA-X} \quad (I)$$

where

C stands for the cysteine radical;

AMBA is the radical of an aminomethylbenzoic acid; and

X is the radical of an amino acid, preferably Met or Phe, although for certain purposes, other amino acids, e.g. Lys, Glu, Cys or Leu, may also be used. Any other natural or unnatural amino acid can also be used at this position.

In a further modification, the AMBA radical may be a heterocyclic acid substituent as described later herein.

The compounds of Formula (I) are different from the prior art farnesyltransferase inhibitors in that they include only two peptide amino acids (C and X) and the single aminomethylbenzoic acid component AMBA which is used as a hydrophobic spacer between the C and X components, i.e., the present compounds do not include separate peptide amino acids $A_1$, $A_2$ as in prior art inhibitors represented by the formula $CA_1A_2X$. The present compounds are consequently free from peptidic amide bonds.

It is also to be noted that the present compounds are not farnesylated by the enzyme. They are, therefore, true inhibitors, not just alternative substrates. This may explain the high inhibitory action of the present compounds relative to their parent compounds which are farnesylated.

A further important feature of the invention is the provision of the compounds of Formula (I) in the form of pro-drugs. Broadly speaking, this is accomplished by functionalizing the terminal end groups (amino, cysteine sulfur and carboxy groups) of the compounds with hydrophobic, esterase-sensitive moieties which serve to increase the plasma membrane permeability and cellular uptake of the compounds and consequently their efficiency in inhibiting tumor cell growth.

The above-mentioned pro-drug aspect of the invention is applicable not only to the compounds of the invention but also to prior peptide inhibitors $CA_1A_2X$ as well as any other peptide with potential for biological uses for the purpose of improving the overall effectiveness of such compounds, as hereinafter described.

In still another modification of the invention, the AMBA component of the compounds of Formula (I) can be replaced by other appropriate spacer elements, particularly non-peptidic amino acids, e.g. aminobenzoic acid, as hereinafter described.

Another important embodiment of the invention contemplates replacing the $A_1A_2X$ portion of the $CA_1A_2X$ tetrapeptide inhibitors with a non-amino acid component while retaining the desired farnesyltransferase inhibiting activity. These compounds may be illustrate by Formula (II):

$$\text{C A} \quad (II)$$

where C is cysteine and A represents an aryl or heterocyclic substituent such as 3-aminomethyl-biphenyl-3'-carboxylic acid, which does not include a peptide amino acid but corresponds essentially in size with $A_1A_2X$, as hereinafter described.

A further modification involves the provision of $CA_1A_2X$ tetrapeptides or C-AMBA-X peptidomimetics which have been modified by functionalizing the sulfhydryl group of the cysteine C with an alkyl phosphonate substituent, as hereinafter described.

Other features of the invention will also be hereinafter apparent.

DESCRIPTION OF PREFERRED EMBODIMENTS

The peptidomimetics of Formula (I) may be made using procedures which are conventional in the art. Preferably the aminomethylbenzoic acid is 3-aminomethylbenzoic acid although 2- or 4-aminomethylbenzoic acid or constrained derivatives such as tetrahydroisoquinoline-7-carboxylic acid, 2-aminomethyl pyridine-6-carboxylic acid or other heterocyclic derivatives, may also be used. This acid component is conveniently reacted with cysteine so that the amino group of the aminomethylbenzoic acid and the cysteine carboxyl group react to form an amido group, other reactive substituents in the reactants being suitably protected against undesired reaction. The amino acid represented by X, preferably Met, is then reacted through its amino group with the deprotected carboxyl group of the aminobenzoic acid. Following deprotection of other reactive groups, the compound of Formula (I) is obtained.

As an alternative, the aminomethylbenzoic acid may first be reacted with the X amino acid followed by reaction with the cysteine component using conventional reaction conditions.

The invention also includes the pharmaceutically acceptable salts of the compounds of Formula (I). These may be obtained by reacting the free base or acid with the appropriate amount of inorganic or organic acid or base, e.g. an alkali metal hydroxide or carbonate, such as sodium hydroxide, an organic amine, e.g. trimethylamine or the like. Acid salts include the reaction products obtained with, for example, toluene sulfonic acid, acetic acid, propionic acid or the like as conventionally used in the art.

The compounds of the invention may be used to inhibit p21ras farnesyltransferase in any host containing the same. This includes both in vitro and in vivo use. Because the compounds inhibit farnesyltransferase, notably human tumor p21ras farnesyltransferase, and consequently inhibit the farnesylation of the oncogene protein ras, they may be used in the treatment of cancer or cancer cells. It is noted that many human cancers have activated ras and, as typical of such cancers, there may be mentioned colorectal carcinoma, myeloid leukemias, exocrine pancreatic carcinoma and the like.

The compounds of the invention may be used in pharmaceutical compositions of conventional form suitable for oral, subcutaneous, intravenous, intraperitoneal or intramuscular administration to a mammal or host. This includes, for example, tablets or capsules, sterile solutions or suspensions comprising one or more compounds of the invention with a pharmaceutically acceptable carrier and with or without other additives. Typical carriers for tablet or capsule use include, for example, lactose or corn starch. For oral compositions, aqueous suspensions may be used with conventional suspending agents, flavoring agents and the like.

The amount of inhibitor administered to obtain the desired inhibitory effect will vary but can be readily determined. For human use, daily dosages are dependent on the circumstances, e.g. age and weight. However, daily dosages of from 0.1 to 20 mg per kg body weight may be mentioned for purposes of illustration.

BRIEF DESCRIPTION OF THE DRAWINGS

FIGS. 3A and 3B compare peptide and peptidomimetic farnesylation activity; while

Figure 1:
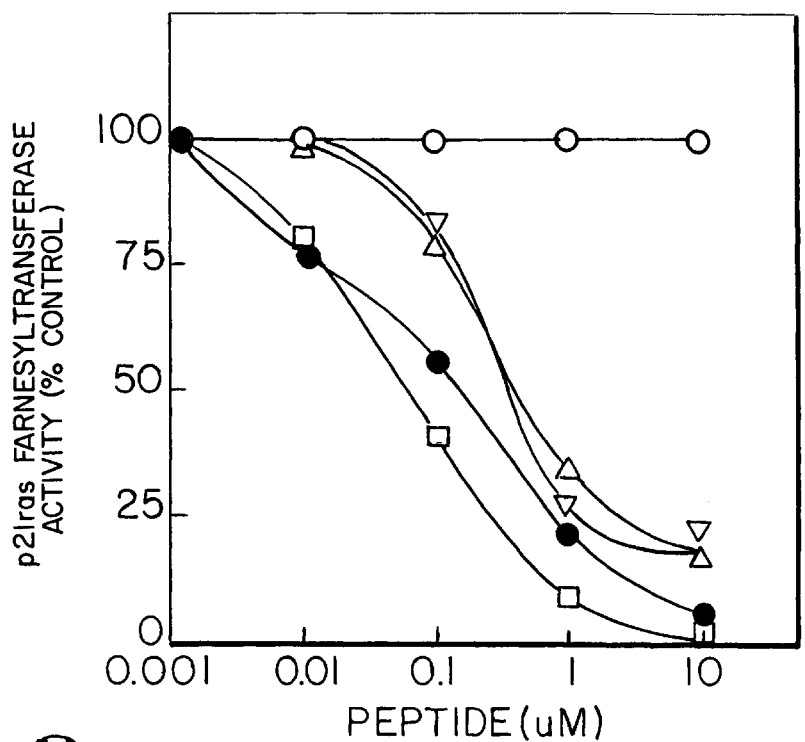
FIGS. 1 and 2 graphically illustrate inhibition results with representative peptides and the present peptidomimetics against human colon carcinoma p21ras farnesyltransferase.

The various aspects of the invention are further described by reference to the following examples. These examples illustrate, among other things, the preparation of the present peptidomimetics and compounds compared therewith. Broadly described, the preparation comprises reaction of the amino acid methyl esters and 3-chloromethylbenzoyl chloride (with $Et_3N$) The resultant 3-chloromethylbenzoylamino acid methyl esters are converted to the corresponding amines by heating with $NaN_3$ in DMSO at 80° C., followed by hydrogenation using a catalytic 5% palladium on carbon under $H_2$ atmosphere. Coupling of this amine with N,S-dibenzyloxycarbonylcysteine using DCC in dichloromethane at room temperature gives the fully protected tetrapeptide analogs. These are deprotected by sequential treatment with $CH_3ONa$ in anhydrous methanol, followed by aqueous methanol to give the N—CBZ protected derivative and then HBr in anhydrous acetic acid at 0° C. to form the target tetrapeptide analogs. All of the compounds which are exemplified demonstrate NMR and mass spectroscopic data consistent with their assigned structures.

EXAMPLE 1

(a) N S-DiCBZ-cysteine

Cysteine HCl (2.0 g, 12.6 mmol) was dissolved in 2N NaOH and benzyl chloroformate (4.5 mL) was slowly added over 15 min. The pH value of the solution was kept at 9–10 by addition of 2 N NaOH (~7 mL) at 0° C. After vigorous stirring for 1 h at 0° C., the aqueous solution was acidified with 2N HCl at pH ~2 to form a colorless syrup. The aqueous solution was decanted and the sticky syrup was triturated with petroleum ether (100 ml×3) to give N,S-diCBZ-cysteine (3.94 g, 80%) as a white solid. Analytically pure sample could also be obtained by flash chromatography (on silica gel, 5% $CH_3OH$ in EtOAc):mp.93°–94° C.; $^1$H NMR ($CDCl_3$) δ7.33 (10H, m), 5.67 (1H, d, J=7.7 Hz), 5.21 (2H, s), 5.12 (2H, s), 4.66 (1H, ddd, J=7.7, 6.7, 4.4 Hz), 3.31 (1H, dd, J=6.7, 14.5 Hz).

(b) [3(Chloromethyl)benzoyl]-Met-$OCH_3$

To a solution of methionine methyl ester hydrochloride (2.0 g, 10 mmol) and 3-(chloromethyl)benzoyl chloride (2.08 g, 11.0 mmol) in methylene chloride (50 mL) was slowly added triethylamine (3.07 mL, 22.0 mmol) at ice bath temperature for 2 hours. The mixture was washed with 0.5N HCl (50 mL×2), brine solution (50 mL×2) and water (50 mL×2). The organic phase was dried over anhydrous $MgSO_4$ and concentrated under reduced pressure. The residues were purified by flash column chromatography (30% EtOAc in hexanes) to give the pure coupled product (3.03 g, 96%) as a white solid: mp. 82°–83° C.; $^1$H NMR ($CDCl_2$) δ7.82 (1H, s), 7.74 (1H, d, J=7.7 Hz), 7.53 (1H, d, J=7.7 Hz), 7.42 (1H, t, J=7.7 Hz), 7.06 (1H, br d, J=7.6 Hz), 4.92 (1H, ddd, J=7.6, 7.1, 5.1 Hz), 4.59 (2H, s), 3.78 (3H, s), 2.58 (2H, t, J=7.1 Hz), 2.26 (1H, m), 2.15 (1H, m), 2.10 (3H, s);

$^{13}$C NMR ($CDCl_3$) δ172.59, 166.54, 138.13, 134.25, 131.95, 129.12, 127.42, 126.97, 52.72, 52.14, 45.55, 31.47, 30.12, 15.55.

(c) [3-(Azidomethyl)benzoyl]-Met-$OCH_3$

A suspension of [3-(chloromethyl)benzoyl]-Met-$OCH_3$ (1.58 g, 5.0 mmol) and sodium azide (1.3 g, 20.0 mmol) in DMSO (40 mL) was stirred at 80° C. for 7 h. The mixture was diluted with methylene chloride (100 mL), washed with brine (70 mL×2) and water (70 mL×2), and then dried over anhydrous $MgSO_4$. The solvent was evaporated under reduced pressure to give slightly yellow residues. The residues were chromatographed on silica gel (30% EtOAc in hexanes) to provide the pure azide (1.45 g, 91%) as a colorless solid: mp. 48°–49° C.; $^1$H NMR ($CDCl_3$) δ7.78 (2H, m), 7.49 (2H, m), 6.99 (1H, br d, J=7.4 Hz), 4.94 (1H, ddd, J=7.4, 7.1, 5.2 Hz), 4.42 (2H, s), 3.80 (3H, s), 2.60 (2H, t, j=7.4 Hz), 2.29 (1H, m), 2.17 (1H, m), 2.12 (3H, s); $^{13}$C NMR ($CDCl_3$) δ177.50, 166.54, 135.97, 134.06, 131.18, 128.89, 126.84, 126.71, 54.09, 52.47, 51.95, 31.18, 30.00, 15.30.

(d) N, S-DiCBZ-Cys-AMBA-Met-$OCH_3$

A suspension of the azide (1.29 g, 4.0 mmol) and 5% palladium on carbon (0.2 g) in methanol (40 mL) was stirred under a hydrogen atmosphere (1 atm) for 2 days at room temperature. The catalyst was removed by filtration through celite (1.5 g), and the solvent was evaporated in vacuo. The residues were evaporated with $H_2O$ (5 mL) twice, giving [3-(aminomethyl)benzoyl]Met-$OCH_3$ (1.12 g, 94%) as a colorless foam: $^1$H NMR ($CDCl_3$) δ7.81 (1H s), 7.68 (1H d, J=7.4 Hz), 7.45 (1H d, J=6.5 Hz), 7.36 (1H t. J=7.4 Hz), 4.91 (1H ddd, J=7.3, 7.1, 5.1 Hz), 3.90 (2H, s), 3.77 (3H, s), 3.21 (2H, br s), 2.59 2H, t, J=7.4 Hz), 2.20 (1H, m), 2.12 (1H m), 2.09 (3H, s).

The above hydrogenated product was dissolved in dry methylene chloride (40 mL) and was added into a solution of N,S-diCBZ-cysteine (1.7 g, 4.4 mmol) and HOBT (0.65 g, 4.8 mmol) in methylene chloride, and then dicyclohexylcarbodiimide (0.91 g, 4.4 mmol) was added at ice bath temperature. The mixture was stirred overnight at room temperature. The resulting dicyclohexylurea was filtered off on celite pad, and the filtrate was washed with 0.5N HCl (50 mL×2), sat. $NaHCO_3$ (50 mL×2) and water (50 mL×2). The organic phase was dried over anhydrous $MgSO_4$ and concentrated under reduced pressure. The residue was purified by flash column chromatography (silica gel, 60% EtOAc in hexanes) to give the desired tetrapeptide analogue (2.01 g, 75% overall yield from the starting azide) as a white solid: mp. 103°–104° C.; $^1$H NMR ($CDCl_3$) δ7.77 (1H, d, J=5.8 Hz), 7.68 (1H, s), 7.58 (1H, d, J=7.5 Hz), 7.39–7.24 (12H, m), 7.05 (1H, br s), 6.17 (1H, br d, J=7.3 Hz), 5.19 (2H, s), 4.97 (1H, d, J=13.0 Hz), 4.94 (1H, ddd, J=7.4, 7.1, 5.0 Hz), 4.82 (1H, d, j=13.0 Hz), 4.53 (1H, dd, J=7.3, 5.0, 4.7 Hz), 4.42 (1H, dd, J=14.6, 5.8 Hz), 4.31 (1H, dd, J=14.6, 4.9 Hz), 3.75 (3H, s), 3.35 (1H, dd, J=14.4, 5.0 Hz), 3.26 (1H, dd, J-14.4, 7.4 Hz), 2.25 (1H, m), 2.17 (1H m), 2.10 (3H, s);$^{13}$C NMR ($CDCl_3$) δ173.60, 170.64, 170.42, 166.70, 156.60, 137.15, 135.84, 134.74, 133.64, 131.79, 129.03–127.50 (12C), 126.43, 69.41, 67.00, 54.75, 52.63, 52.09, 44.12, 33.36, 31.20, 30.39, 15.41.

EXAMPLE 2

Example 1 was repeated except that, in (b), phenylalanine methyl ester hydrochloride was used to give N,S-DiCBZ-Cys-AMBA-Phe-$OCH_3$ characterized as follows: mp. 149°–150° C.; $^1$H NMR ($CDCl_3$) δ7.63 (2H, m), 7.38–7.23 (15H, rm), 7.21–7.17 (3H, m), 6.94 (1H, m), 6.04 (1H br d, J=7.2 Hz), 5.19 (2H, s), 5.05 (1H, ddd, J=7.2, 7.1, 6.0 Hz), 4.99 (1H, d, J=14.6 Hz), 4.96 (1H, d, J=14.6 Hz), 4.52 (1H, ddd, J=7.4, 6.4, 5.0 Hz), 4.39 (1H, dd, J=14.4, 6.0 Hz), 4.37 (1H, dd, J=14.4, 4.9 Hz), 3.73 (3H, s), 3.38 (1H dd, J=14.6, 5.8 Hz), 3.36 (1H, dd, J=14.4, 7.4 Hz), 3.27 (1H dd J=14.4, 5.0 Hz), 3.23 (1H, dd, J=14.6, 7.0 Hz); $^{13}$C NMR ($CDCl_3$) δ173.23, 170.91, 170.32, 166.60, 156.64, 137.51, 136.41, 135.97, 134.81, 133.84, 131.59, 129.31–127.98 (16C), 127.10, 126.51, 69.57, 67.16, 54.93, 54.13, 52.55, 43.98, 37.67, 33.39.

EXAMPLE 3

Example 1 was repeated except that, in (b), the leucine derivative was used in place of the methionine starting material. This gave N,S-DiCBZ-Cys-AMBA-Leu-$OCH_3$ characterized by: mp. 112°–114° C.; $^1$H NMR ($CDCl_3$) δ7.74 (1H d, J=7.5 Hz), 7.66 (1H s), 7.36–7.23 (14H, m), 6.35 (1H, br d, J=7.9 Hz), 5.18 (2H, s), 4.93 (1H d, J=12.3 Hz), 4.84 (1H, ddd, J=7.9, 7.8, 4.9 Hz), 4.74 (1H, d, J=12.8 Hz), 4.58 (1H, ddd, J=7.4, 6.2, 5.3 Hz), 4.37 (1H, dd, J=14.4, 5.6 Hz), 4.20 (1H, dd, J=14.4, 4.4 Hz), 3.72 (3H, s), 3.35 (1H, dd, J=14.3, 5.3 Hz), 3.28 (1H, dd, J=14.3, 7.4 Hz), 1.75 (3H, m), 0.98 (3H, d, J=5.8 Hz), 0.96 (3H, d, J=6.0); $^{13}$C NMR (CDCl$_3$) δ174.76, 170.95, 170.24, 166.72, 156,62, 137.34, 135.97, 134.82, 133.77, 131.69, 129.11–127.99 (11C), 127.39, 126.43, 69.54, 67.15, 67.15, 54.99, 52.50, 51.44, 44.04, 40.96, 33,38, 25.06, 23.01, 21.74.

EXAMPLE 4

Example 1 was repeated except that, in (b), the lysine derivative was used in place of the methionine starting material. This gave N,S-DiCBZ-Cys-AMBA-Lys-OCH$_3$ characterized by: mp. 88°–89° C.; $^1$H NMR (CDCl$_3$) δ7.77 (1H, d, J=6.4 Hz), 7.68 (1H, s), 7.36–7.25 (13H, m), 7.07 (1H, br s), 6.16 (1H, d, J=6.5 Hz), 5.20 (2H, s), 4.98 (1H, d, J=12.2 Hz), 4.84 (1H, d, J=12.2 Hz), 4.77 (1H ddd, J=8.0, 7.9, 5.0), 4.66 (1H, br t, J=7.3 Hz), 4.53 (1H, ddd, J=7.4, 6.5, 5.4 Hz), 4.43 (1H, dd J=14.2, 6.0 Hz), 4.35 (1H, dd, J=14.2, 4.5 Hz), 3.74 (3H, s), 3.37 (1H, dd, J=14.4, 5.4 Hz), 3.27 (1H, dd, J=14.4, 7.4 Hz), 3.09 (2H, m), 1.89 (2H, m), 1.47 (4H, m), 1.38 (9H, s); $^{13}$C NMR (CDCl$_3$) δ173.92, 170.83, 170.31, 166.86, 162.56, 156.55, 156.06, 137.48, 135.94, 134.78, 133.86, 131.57, 129.01–127.88 (11C), 127.26, 126.41, 69.47, 67.03, 54.90, 52.73, 52.51, 43.93, 40.05, 36.49, 33.33, 31.47, 29.44, 28.38 (3C), 22.90.

EXAMPLE 5

Example 1 was repeated except that, in (b), the glutamine derivative was used in place of the methionine starting material. This gave N,S- DiCBZ-Cys-AMBA-Glu-OCH$_3$ characterized by: mp. 99°–101° C.; $^1$H NMR (CDCl$_3$) δ7.76 (1H, d, J=5.7 Hz), 7.68 (1H, s), 7.38–7.26 (13H, m), 6.91 (1H, br s), 6.18 (1H, d, J=7.8 Hz), 5.20 (2H, s), 4.98 (1H, d, J=12.5 Hz), 4.85 (1H, d, J=12.5 Hz,), 4.78 (1H ddd, J=8.1, 8.0, 5.8 Hz), 4.51 (1H, ddd, J=7.8, 7.4, 5.0 Hz), 4.38 (1H, dd, J=14.4, 5.9 Hz), 4.29 (1H, dd, J-14.4, 4.8 Hz), 3.74 (3H, s), 3.63 (3H, s), 3.37 (1H, dd, J=14.4, 4.9 Hz), 3.27 (1H, dd, J=14.4, 7.5 Hz), 2.49 (2H, m), 2.34 (1H, m), 2.17 (1H, m); $^{13}$C NMR (CDCl$_3$) δ173.53, 172.88, 171.16, 170.10, 166.89, 156.58, 137.84, 135.94, 134.78, 133.80, 131.39, 129.08–128.00 (11C), 126.97, 126.28, 69.61, 67.25, 55.19, 52.66, 52.37, 51.93, 43.60, 33.18, 30.40, 26.96.

EXAMPLE 6

Example 1 was repeated except that N-fmoc-S-tritylserine was prepared and used in lieu of N,S-DiCBZ-cysteine.

The resulting N-fmoc-S-trityl-Ser-AMBA-Met-OCH$_3$ was characterized as follows: mp. 109°–110° C.; $^1$NMR (CDCl$_3$) δ7.78–7.73 (4H, m), 7.68–7.46 (3H, m), 7.43–7.31 (4H, m), 7.30–7.21 (2H, m), 7.14 (1H, br s), 6.17 (1H, d, J=6.0 Hz), 4.92 (2H, m), 4.47 (2H, m), 4.37 (2H, m), 4.20 (1H, br t, J=7.6 Hz), 4.12 (2H, m), 3.78 (3H, s), 2.60 (2H, t, J=7.4 Hz), 2.23 (2H, m), 2.10 (3H, s), 1.14 (6H, s); $^{13}$C NMR (CDCl$_3$) δ173.10, 170.79, 166.70, 156.44, 143.93, 143.63, 141.30 (2C), 138.18, 134.07, 131.26, 129.01, 127.25 (2C), 127.07 (2C), 126.85, 126.54, 125.25, 125.03, 120.01 (2C), 74.11, 67.09, 62.07, 54.82, 52.67, 52.18, 46.98, 43.73, 31.44, 30.31, 29.39 (3C), 15.55.

EXAMPLE 7
Preparation of Cys-AMBA-Met-OH-HBr

To a solution of the protected tetrapeptide analog of Example 1 (i.e. N,S-diCBZ-Cys-AMBA-Met-OCH$_3$) (0.67 g, 1.0 mmol) in anhydrous CH$_3$OH (40 Ml) was added cautiously NaOCH$_3$ (0.27 g, 5.0 mmol) at ice-bath temperature, then the mixture was stirred for an additional 1 hr. at ice-bath temperature. The reaction mixture was evaporated under reduced pressure until a total volume of 10 Ml, diluted with H$_2$O (20 Ml) and washed with EtOAc (30 mL×2). The aqueous phase was acidified with 2N HCl at pH ~2 to precipitate a white solid. The solid was collected by filtration, washed with H$_2$O (20 mL×3) and ether (20 mL×2), and dried in vacuo to give a white solid (0.47 g, 91%) containing the N-CBZ protected analog: mp. 89°–90° C.; $^1$H NMR (CD$_3$OD) δ7.68 (1H s), 7.63 (1H d, J=7.6 Hz), 7.31 (2H, m), 2.79–7.16 (5H, m), 4.99 (2H, s), 4.64 (1H ddd, J=7.3, 7.0, 4.7 Hz), 4.35 (2H, d, J=5.2 Hz), 4.17 (1H dd J=6.5, 6.1H), 2.76 (2H, m), 2.52 (2H, m), 2.10 (1H m), 2.04 (1H, m), 1.98 (3H, s).

The above N-CBZ blocked tetrapeptide analog was dissolved in glacial acetic acid (4 Ml) and then treated with 33% HBr in acetic acid (4 Ml) at ice-bath temperature for 25–40 min. The mixture was concentrated until a total volume of 4 mL and anhydrous Et$_2$O (40 mL) was added to precipitate a white solid. This solid was collected by centrifugation, washed twice with anhydrous Et$_2$O (20 mL), and dried in vacuo to give the pure tetrapeptide hydrobromide salts (0.31 g, 66% overall yield from fully protected tetrapeptide analog) as a white hydroscopic solid: Decomp. 149°–152° C.; 1H NMR (CD$_3$OD) δ7.70 (1H, m), 7.63 (1H m), 7.38 (1H m), 7.30 (1H m), 4.64 (1H, m), 4.36 (2H, d, J=5.0 Hz), 4.18 (1H m), 2.94–2.84 (2H, m), 2.49 (2H, m), 2.09 (1H m), 1.97 (1H m), 1.96 (3H, s).

EXAMPLE 8

The following were prepared using the procedure of Example 7 with appropriate replacement of the cysteine or methionine component as indicated:

Cys-AMBA-Phe-OH.HBr: Decomp. 169°–170° C.; $^1$H NMR (CD$_3$OD) δ7.56 (1H m), 7.45 (1H, m), 7.33 (1H, m), 7.22 (1H, m), 7.10 (4H, m), 4.68 (1H m), 4.29 (2H, br s), 4.19 (1H m), 3.11–2.86 (4H, m).

Cys-AMBA-Leu-OH.HBr: Decomp. 148°–150° C.; H NMR (CD$_3$OD) δ7.69 (1H m), 7.61 (1H m), 7.38 (1H, m), 7.28 (1H, m), 4.53 (1H, m), 4.34 (2H, br s), 3.94 (1H, m), 3.01–2.96 (2H, m), 1.61 (3H, m), 0.84 (6H, br s).

Cys-AMBA-Glu-OH.HBr: Decomp. 135–137° C.; $^1$H NMR (CD$_3$OD) δ7.69 (1H, m), 7.61 (1H, m), 7.39 (1H, m), 7.30 (1H, m), 4.49 (1H, m), 4.34 (1H, br s), 3.96 (1H,m), 3.02–2.77 (2H,m), 2.52 (2H, m), 2.35 (1H, m), 1.88 (1H m).

Cys-AMBA-Lys-OH.HBr: Decomp. 182°–184° C.; $^1$H NMR (CD$_3$OD) δ7.74 (1H, d, J=7.6 Hz), 7.64 (1H, m), 7.41 (1H, d, J=7.6 Hz), 4.46 (1H, ddd, J=9.2, 5.0, 4.8 Hz), 4.86 (2H, d, J=6.9 Hz), 3.98 (1H, ddd, J=7.4, 6.4, 5.7 Hz), 2.97 (1H, dd, J=14.6, 5.7 Hz), 2.84 (1H, dd, J=14.6, 7.4 Hz), 2.82 (2H, t, J=7.3 Hz), 1.80 (2H, m), 1.59 (2H, m), 1.43 (2H, m).

Cys-AMBA-Met-OH.HBr: Decomp. 106°–108° C.; $^1$H NMR (CD$_3$OD) δ7.72 (1H, s), 7.66 (1H, d, J=7.6 Hz), 7.43 (1H, d, J=7.6 Hz), 7.34 (1H, t, J=7.6 Hz), 4.69 (1H, dd, J=7.8, 5.0 Hz), 4.40 (2H, d, J=6.8 Hz), 3.94 (1H, dd, J=5.1, 4.3 Hz), 3.92 (1H, dd, J=11.6, 4.0 Hz), 3.79 (1H dd, J=11.6, 6.1 Hz), 2.51 (2H, m), 2.10 (2H, m), 2.00 (3H, s).

EXAMPLE 9
p21ras Farnesyltransferase Activity Assay

Human colon carcinoma COLO-205 cells (ATCC, Rockville, Md.) were grown to confluency in RPMI containing 10% FBS, 1% penicillin/streptomycin at 37° C and 10% Co$_2$ atmosphere. The cells were homogenized in lysis buffer (10 mM Hepes pH 7.4, 1 mM MgCl$_2$, 1 mM EDTA, 0.1 mM DDT, and 0.1 mM PMSF) and centrifuged at 12,000×g followed by a 60,000×g centrifugation of the supernatant. p21ras farnesyltransferase from 60,000×g supernatant fractions was then partially purified by DEAE-sephacel chromatography where it was eluted with 50 mM Tris (pH 7.5) containing 0.4M NaCl. p21ras farnesyltransferase activity was determined by measuring the amount of [3H]FPP transferred to recombinant p21H-ras as previously described (15,16). p21H-ras was isolated from E. coli strain RRI expressing p21H-ras (Hoffman-LaRoche, Inc.) as described previously (25) except for the last step of purification where HPLC was replaced by DEAE-sephacel chromatography. For peptide inhibition studios, CA$_1$A$_2$X peptides and peptidomimetics were premixed with p21ras farnesyltransferase (40 μg) prior to adding the reaction mixture (50 Mm Tris (pH. 7.5), 50 μM ZnCl$_2$, 20 mM KCl, 1 mM DTT, 20 μM p21H-ras, 9 mmol [3H]FPP). After incubation for one hour at 37° C., the reaction was stopped and filtered on glass fibers as described earlier (15,16). Control samples containing no peptides had a p21ras farnesyltransferase activity of 9.63 fmole/μg×hr corresponding to 7850 cpm per filter. The results for C-AMBA-M (□), CVIM (●), CIIM (Δ), CVVM (∇) and VCIM (○) are indicated in FIG. 1. The data presented is representative of three independent experiments.

Figure 2:
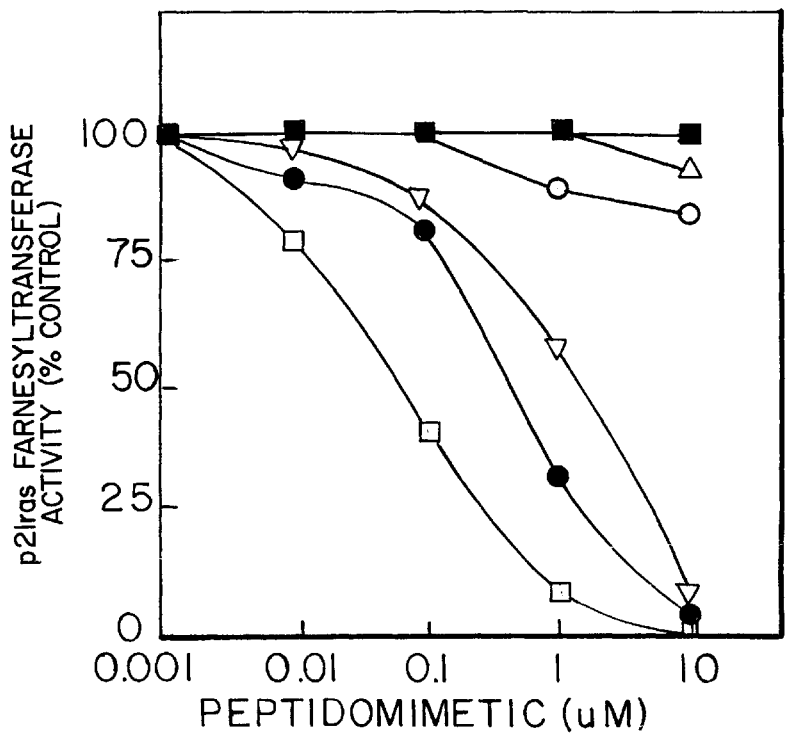

FIG. 2 compares the results obtained with the following compounds: C-AMBA-M (□), C-AMBA-F (●), C-AMBA-E (∇), C-AMBA-K (○), C-AMBA-L (Δ) and S-AMBA-M (■), where the data presented is representative of at least two independent experiments.

Farnesylation of CA$_1$ A$_2$X Tetrapeptides and Peptidomimetics

The ability of human colon carcinoma COLO-205 p21ras farnesyltransferase to farnesylate various peptides and peptidomimetics was determined as described previously (22). Briefly, the reaction mixture (50 mM Tris-HCl (pH 7.5), 50 μM ZnCl$_2$, 3 mM MgCl$_2$, 20 mM KCl, 1 mM DTT, 0.2% (V/V) octyl β-D glucoside, 15 pmoles of [$^3$H]FPP, 3.6 μM peptide and 20 μg partially purified p21ras farnesyltransferase) was incubated for 30 min. at 37° C., then spotted onto baked silica gel G TLC sheets (20×20 cm, Brinkmann Instruments) and developed with n-propylalcohol/ammonium hydroxide/water (6:3:1). Silica sheets were exposed to x-ray film for detection of [$^3$H]-farnesyl-peptides.

Figure 3A:
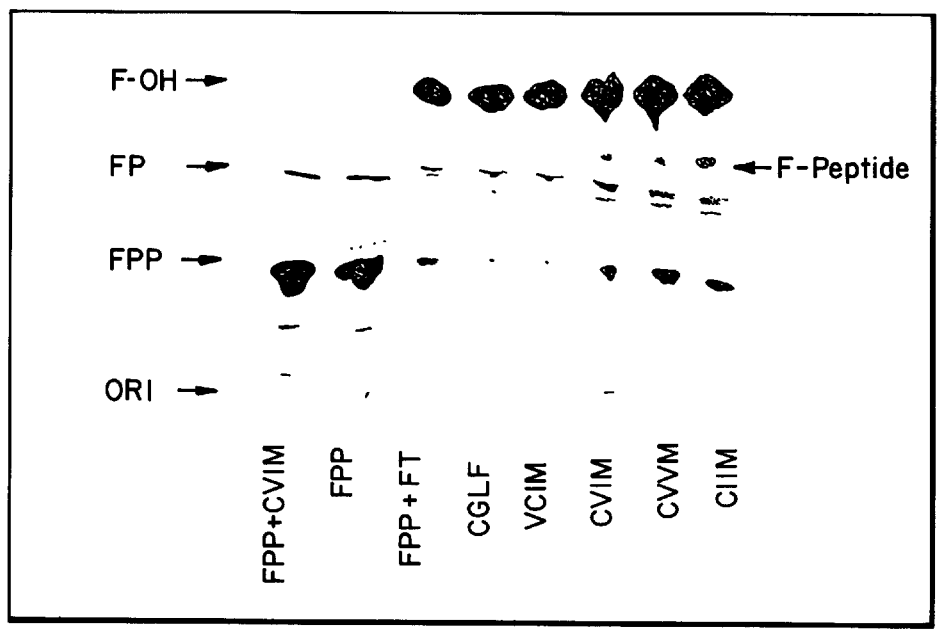
Figure 3B:
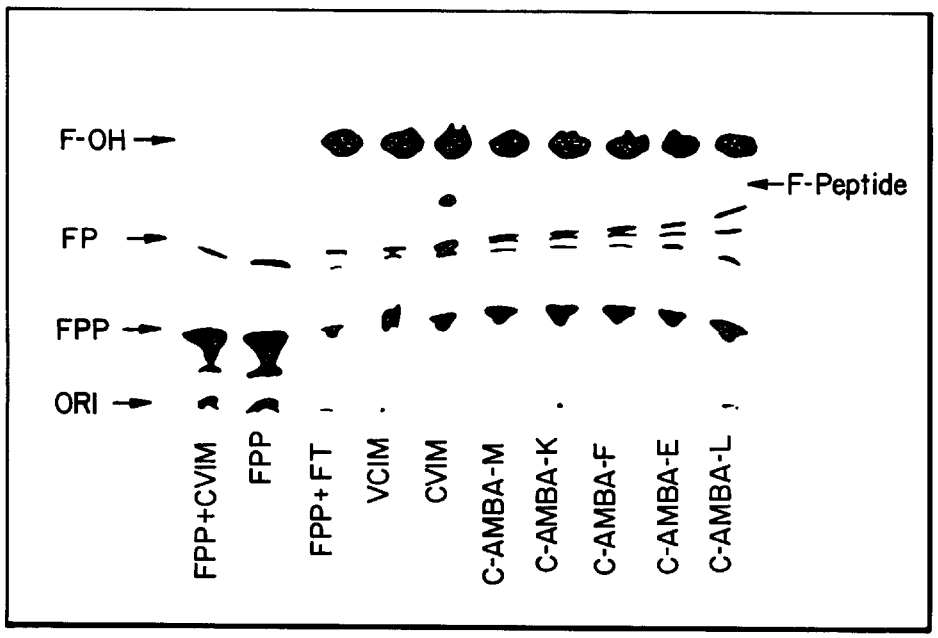

Results are shown in FIGS. 3A and 3B wherein FPP, FP, F-OH, FT and F-peptide designate farnesylprophosphate, farnesylmonophosphate, farnesol, farnesyltransferase and farnesylated peptide, respectively. Control samples contained from left to right, respectively: only FPP and CVIM but no enzyme in the reaction mixture; only FPP; FPP and enzyme (FT) but no peptide. All remaining lanes correspond to reaction mixtures that contained enzyme, FPP and indicated tetrapeptide or peptidomimetic. For each sample, data is representative of at least two independent experiments.

EXAMPLE 10

To determine the potency of the novel peptidomimetics relative to their parent tetrapeptides, the potency of CA$_1$A$_2$X corresponding to the carboxyl terminus ends of p21 K$_A$-ras, p21 K$_B$-ras and p21N-ras to inhibit p21ras farnesyltransferase from human colon carcinoma (COLO-205) and Burkitt's lymphoma (Daudi) was determined. CVIM (0–10 μM) which corresponds to the last four carboxyl terminus amino acids of p21 K$_B$-ras was found to inhibit p21ras farnesyltransferase activity from COLO-205 and Daudi tumor cells in a dose dependent manner with IC$_{50}$ values of 200 nM and 190 nM, respectively (FIG. 1 and Table 1).

VCIM, a tetrapeptide (SEQ ID NO:5) where the cysteine and valine are switched and, therefore, contains no cysteine at the fourth position from the carboxyl terminus, did not inhibit p21ras farnesyltransferase with concentrations as high as 10 μM (FIG. 2) and Table 1).

S-farnesylated CVIM (F-CVIM), corresponding to the product of the enzymatic reaction (27,28), did not inhibit p21ras farnesyltransferase (Table 1). In contrast, CIIM and CVVM (SEQ ID NO:6 and SEQ ID NO:7), the carboxyl terminus tetrapeptides of p21 K$_A$-ras and p21N-ras, inhibited the enzyme with IC$_{50}$ values of 0.83 and 0.61 μM (Daudi) and 0.53 and 0.46 μM (COLO-205), respectively (FIG. 2 and Table 1).

The tetrapeptide mimetic Cys-AMBA-Met (0–10 μM) of the invention, where the AMBA substituted for "VV", "II" and a "VII" in CVVM, CIIM and CVIM inhibited COLO-205 and Daudi p21ras farnesyltransferase in a dose dependent manner with IC$_{50}$ values of 60 nM and 120 nM, respectively (FIG. 3 and Table 1). This corresponds to an increase in potency for Cys-AMBA-Met of 3.3-, 7.7- and 8.8- (COLO-205) and 1.6-, 5.1- and 6.9- (Daudi) fold over CVIM, CVVM and CIIM, respectively (Table 1). Thus, despite lacking the A$_1$A$_2$ dipeptide, the AMBA-containing peptidomimetics of the invention, particularly the C-AMBA-Met compound, are potent inhibitors of p21ras farnesyltransferase from human tumors.

TABLE 1

Inhibition of p21ras farnesyltransferase by CA$_1$A$_2$X and corresponding peptidomimetics

| | IC$_{50}$ (μM) | |
|---|---|---|
| Peptidomimetics | COLO-205 | Daudi |
| CVIM | 0.20 | 0.19 |
| CIIM | 0.53 | 0.83 |
| CVVM | 0.46 | 0.61 |
| VCIM | >10 | >10 |
| C-AMBA-M | 0.06 | 0.12 |
| C-AMBA-F | 0.53 | 0.60 |
| C-AMBA-E | 1.42 | 1.54 |
| C-AMBA-K | >10 | >10 |
| C-AMBA-L | >10 | >10 |
| S-AMBA-M | >10 | >10 |
| F-CVIM | N.D.* | >10 |

Partially purified p21ras farnesyltransferase from human tumors (COLO-205 and Daudi) were premixed with various tetrapeptides and peptidomimetics and assayed for their ability to transfer farnesyl to recombinant p21 H-ras.
*Not Determined.

The foregoing results indicate that a central peptide bond as in the case of the CA$_1$A$_2$X tetrapeptides is not essential for strong binding hydrophobic is required for recognition is a hydrophobic moiety between the cysteine and methionine. The sulfhydryl group in Cys-AMBA-Met is also important since Ser-AMBA-Met did not inhibit p21ras farnesyltransferase (FIG. 3, Table 1). Replacing the methylthioether group of methionine in Cys-AMBA-Met by a negatively charged side chain as in Cys-AMBA-Glu reduced its ability to inhibit the enzyme by 24-fold (COLO-205) and 13-fold (Daudi) and a positively charged side chain at the X-position as in Cys-AMBA-Lys abolished p21ras farnesyltransferase inhibition activity (FIG. 3 and Table 1). However, the Cys-AMBA-Phe tetrapeptide mimetic with an aromatic amino acid, phenylalanine, at the X-position according to the invention, was a potent inhibitor (IC$_{50}$=530 nM (COLO-205) and 600 nM (Daudi) (FIG. 3 and Table 1). Thus, the nature of the X at the carboxyl terminus influences greatly the ability of the AMBA-containing peptidomimetics to inhibit p21ras farnesyltransferase. Amino acids with a neutral side chain are preferred to those with charged ones, with negative charges better tolerated than positive charges. Furthermore, a mimetic with leucine at the X-position, Cys-AMBA-Leu, had no inhibitory activity (FIG. 3, Table 1). This is consistent with previous studies where $CA_1A_2X$ tetrapeptides with leucine at the X-position showed very little farnesyltransferase inhibition but had high geranylgeranyltransferase inhibitory activity (18,21).

$CA_1A_2X$ peptides have been shown to inhibit rat brain p21ras farnesyltransferase by serving as alternative substrates (22,23). FIG. 3A shows that COLO-205 human tumor p21ras farnesyltransferase farnesylated CVIM, CVVM and CIIM but not VCIM which lacks a cysteine at the 4th position from the carboxyl terminus. Similarly, CGLF, the carboxy terminal tetrapeptide of the α subunit of Gi which is known not to be farnesylated in vivo, was not farnesylated by human tumor farnesyltransferases (FIG. 3A). Replacing the $A_1$ and $A_2$ by AMBA prevented p21ras farnesyltransferase from farnesylating the SH group of cysteine (FIG. 3B).

None of the tetrapeptide mimetics of the invention appears to be farnesylated by human tumor COLO-205 p21ras farnesyltransferase (FIG. 3B). Similar results have been obtained with human tumor Daudi p21ras farnesyltransferase. Thus, although it is found that the peptidomimetic Cys-AMBA-Met is a much more potent inhibitor than its natural parent peptides CIIM, CVIM and CVVM, the peptidomimetic was not farnesylated by p21ras farnesyltransferase. This indicates that although isoleucine and valine are not required for peptide binding and inhibitory activity, they promote farnesylation. It is also possible that the structural constraints of the AMBA spacer alter the bound conformation so that the cysteine thiol is no longer at the precise position needed for farnesylation. Replacing Met by Phe, Lys or Glu did not restore the ability of the peptidomimetic to be farnesylated.

The higher potency of the peptidomimetics as compared to their parent $CA_1A_2X$ peptides may be due to this lack of farnesylation since once farnesylated $CA_1A_2X$ peptides are no longer good inhibitors of p21ras farnesyltransferase. See Table 1 and reference (24). A further advantage of the Cys-AMBA-Met inhibitors over the $CA_1A_2X$ tetrapeptides is that they contain no peptidic amide bonds and are, therefore, less likely to be degraded by peptidases.

The compounds referred to in Table 1 may be structurally illustrated as follows, CVIM (the carboxy terminal last four amino acids of p21$K_B$ras) being used as representative of the $CA_1A_2X$ compounds:

CVIM

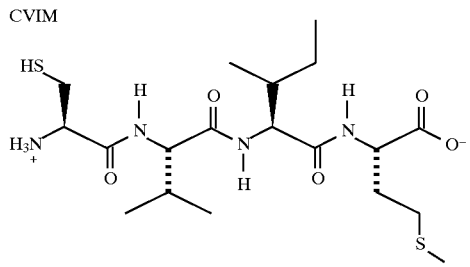

-continued
AMBA Peptidomimetics

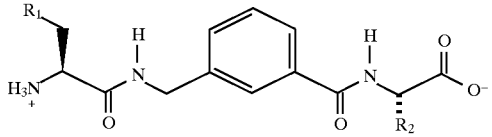

Cys-AMBA-Met. $R_1$=SH, $R_2$=$CH_2CH_2SCH_3$
Cys-AMBA-Phe $R_1$=SH, $R_2$=$CH_2Ph$
Cys-AMBA-Glu. $R_1$=SH, $R_2$=$CH_2CH_2COO$
Cys-AMBA-Lys. $R_1$=SH, $R_2$=$CH_2(CH_2)_2CH_2NH_3^+$
Cys-AMBA-Leu. $R_1$=SH, $R_2$=$CH_2CH(CH_3)_2$
Ser-AMBA-Met. $R_1$=OH, $R_2$=$CH_2CH_2SCH_3$

As shown, C-AMBA-M is a particularly effective inhibitor when compared with the representative $CA_1A_2X$ compounds with C-AMBA-F also demonstrating significant inhibitory activity.

It will be appreciated from the foregoing that the peptidomimetics of the Formula (I) represent modifications of the $CA_1A_2X$ box of p21 $K_A$-ras (CIIM), p21 $K_B$-ras (CVIM) and p21N-ras (CVVM) where the $A_1$ and $A_2$ valines and isoleucines have been replaced by a 3-aminomethylbenzoic acid (AMBA) spacer (26). This group provides a link between the cysteine (C) at the amino terminus and the X (Met or Phe) at the carboxyl terminus that resembles the $A_1A_2$ dipeptide in both distance and hydrophobicity (FIG. 2). However, the present peptidomimetics contain only two instead of three amide bonds, neither of which is peptidic in nature.

Despite the substantial structural alterations in the natural $CA_1A_2X$ inhibitor, the present compounds retain several of the key features required for inhibitory activity. First, the cysteine sulfhydryl group in Cys-AMBA-Met is in the same relative position to the methionine carboxylate as in CVIM. This is important since previous studies have shown that the cysteine residue must be at the fourth, not the third or fifth, position from the carboxyl terminus (15,18). Second, the present peptidomimetics retain their carboxylate negative charge which has been shown previously to be essential for $CA_1C_2X$ p21ras farnesyltransferase inhibition activity (18, 21). Finally, it has been found that the AMBA spacer reproduces the central hydrophobic region of the most effective tetrapeptide inhibitors where $A_2$ is an aromatic residue (18,21).

As a modification of the foregoing, the AMBA component has been replaced by other non-peptide amino acids or other hydrophobic spacer elements that mimic the structure and conformation of CVIM or like tetrapeptides $CA_1A_2X$. A variety of hydrophobic spacers have been used as replacements for AMBA according to this aspect of the invention. This includes, as examples, 3-aminobenzoic acid, 4-aminobenzoic acid and 5-aminopentanoic acid as well as heterocyclic carboxylic acids such as tetrahydroisoquinoline-7-carboxylic acid, 2-aminomethyl pyridine-6-carboxylic acid or the like as mentioned earlier, as replacements for the AMBA component of the Formula (I) compounds. Thus, in a broad sense, the peptidomimetics of the invention may be represented by the Formula (III):

cβx (III)

where C and X have the values given earlier and β stands for the radical of a non-peptide aminoalkyl or amino-substituted aliphatic or aromatic carboxylic acid or a heterocyclic monocarboxylic acid, for example, 3-aminobenzoic acid (3-ABA), 4-aminobenzoic acid (4-ABA) or 5-aminopentanoic acid (5-APA). Representative compounds using 3-ABA, 4-ABA and 5-APA are structurally illustrated as follows:

Derivative of:

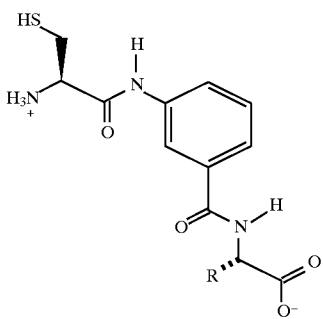

3-ABA

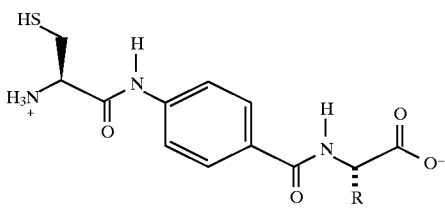

4-ABA

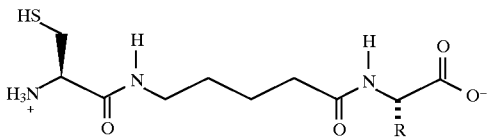

5-APA

Other suitable β substituents which may be mentioned include those obtained by using aminomethyl- or aminocarboxylic acid derivatives of other cyclic hydrophobic compounds such as furan, quinoline, pyrrole, oxazole, imidazole, pyridine and thiazole. Generally speaking, therefore, the β substituent may be derived from any hydrophobic, non-peptidic aminoalkyl- or amino-substituted aliphatic, aromatic or heterocyclic monocarboxylic acid.

According to another aspect of the invention, the $A_1A_2X$ component of the $CA_1A_2X$ tetrapeptide can be replaced entirely by the selection of an appropriate hydrophobic amine-substituted alkyl, aryl or heterocyclic carboxylic acid for direct connection with cysteine C to provide compounds of the Formula (II) as mentioned earlier:

$$CΔ \quad (II)$$

where C is cysteine and Δ represents a hydrophobic amine-substituted alkyl, aryl or heterocyclic carboxylic acid which is not a peptide amino acid but which corresponds essentially in size with $A_1A_2X$. For example, cysteine C and an aminoalkyl-bicyclic aryl-carboxylic acid, e.g. 3-aminomethyl-biphenyl-3-carboxylic acid are linked directly together to give the compound:

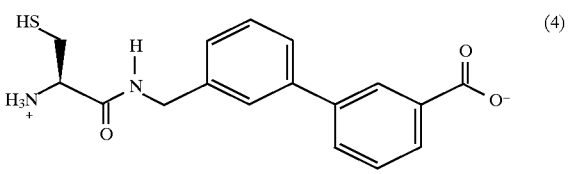

Comparison of compound (4) with CVIM shows that the cysteine sulfur atom and the carboxylate group are maintained in a very similar spatial relationship. Other modifications in Δ which maintain this relationship should give similar inhibitory results.

According to still another feature of the invention, other effective inhibitors for farnesyltransferase may be provided by incorporating a negatively charged residue onto the compounds of Formulas (I), (II) or (III) or the prior tetrapeptides $CA_1A_2X$. This feature of the invention is based on a consideration of the transition state of the farnesylation reaction and the recognition that the functional enzyme complex must involve a farnesyl pyrophosphate binding site close to the peptide binding region. Compounds representative of this embodiment include peptides prepared with a phosphonate residue linked at different distances to the cysteine sulfur. These derivatives have been prepared by reaction of N-Cbz-cysteine with ethyl 2-chloroethylphosphonate followed by condensation with the C-terminal methionine adduct of 3-aminomethylbenzoic acid (or N-deprotected VIM methyl ester). Deprotection of the phosphonate, carboxylate and amino protecting groups gives analogs (5) and (6), respectively, which contain elements of the tetrapeptide and farnesyl pyrophosphate residues and hence are able to interact with binding groups in both recognition sites in p21ras farnesyltransferase:

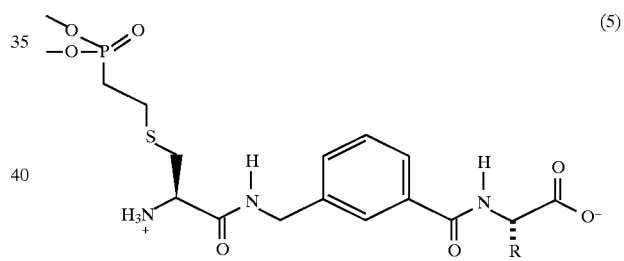

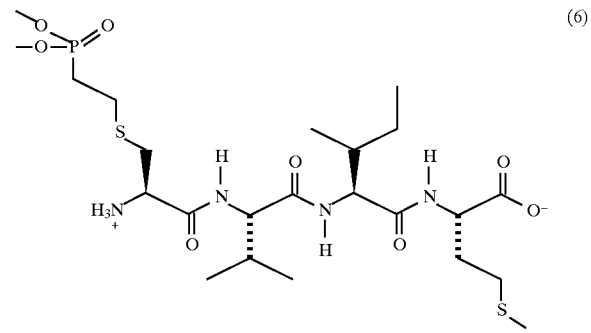

The above described phosphonates as contemplated herein can be structurally represented as follows:

$Δ_1$ - $CA_1A_2X$ $Δ_1$ - C-AMBA-X $Δ_1$-C-β-X or $Δ_1C$-Δ where C, $A_1$, $A_2$, X, AMBA, β and Δ are as previously described and $Δ_1$ is a phosphonate group joined to cysteine through the cysteine sulphur atom.

Another modification of the compounds disclosed herein involves the linking of a benzyl group to the cysteine sulfur in order to mimic the hydrophobic nature of the farnesyl group that would normally be linked to the sulfur atom in the product. Using CVIM as representative, this gives a compound (7) of the following structure:

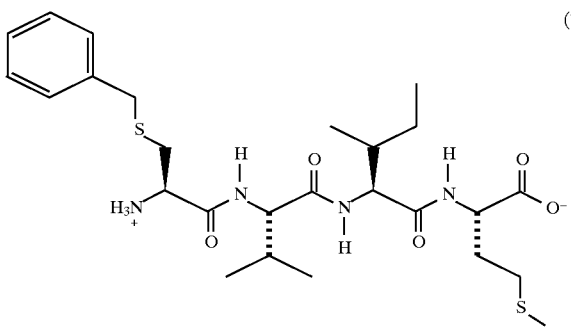

(7)

This benzylated group of compounds can be broadly defined as $β_1CA_1A_2X$, $β_1$C-AMBA-X or $β_1$CΔ where C, $A_1$, $A_2$, X, AMBA and Δ have the meanings given earlier and $β_1$ is aryl or aralkyl, e.g. benzyl.

As indicated earlier, an important further feature of the invention is the modification of the compounds of the invention, as well as the tetrapeptide p21ras farnesyl transferase inhibitors of the formula $CA_1A_2X$, to provide prodrugs. This involves forming lipophilic esterase-sensitive derivatives from the compounds by appropriately functionalizing the terminal groups. For example, the terminal amino groups and the cysteine sulfur can be reacted with benzyl chloroformate to provide carbobenzyloxy ester end groups while the terminal carboxy group at the other end of the compound is converted to an alkyl or aryl ester, e.g. the methyl ester.

It has been found that functionalizing the terminal end groups as described greatly enhances the tumor cell growth inhibitory activity of the peptidomimetics of the invention and the previously known peptides. It is known that peptide uptake into cells is inefficient. Derivatization of the prior peptides $CA_1A_2X$ and the peptidomimetics described herein with lipophilic or hydrophobic, esterase-sensitive moieties increases the plasma membrane permeability and cellular uptake of the compounds and consequently their efficiency in inhibiting tumor cell growth. It is, however, noted that this feature of the invention is not limited to use in inhibiting tumor cell growth but is broadly applicable to improving the efficiency of introducing peptides generally into cells for any desired biological activity.

While the carbobenzyloxy derivatives have been referred to as one way of functionalizing the peptides and peptidomimetics to improve efficiency, it will be appreciated that a variety of other groups may also be used for the purposes noted. Typical alternatives include cholesterolyl, aryl or aralkyl such as benzyl, phenylethyl, phenylpropyl or naphthyl, or alkyl, typically methyl or other alkyl of, for example, up to 8 carbon atoms or more. It is contemplated that such functional groups would be attached to the cysteine sulfur and the terminal amino and carboxy groups.

Using CVIM and C-AMBA-M as representative of prior peptide inhibitors and the present compounds, respectively, the functionalized pro-drug embodiment of the invention may be structurally illustrated as follows:

BBM-C-AMBA-M

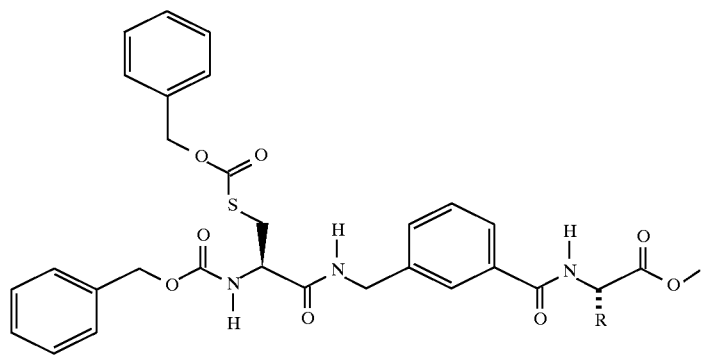

BBM-CVIM

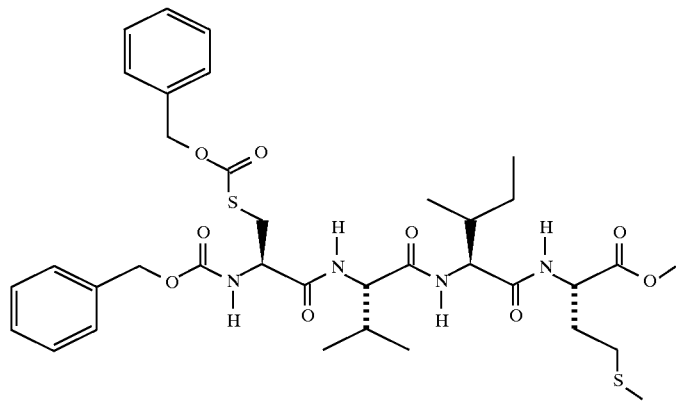

Another very potent tumor cell growth inhibitor is the BBM—derivative of compound (4) above. This derivative may be illustrated as follows:

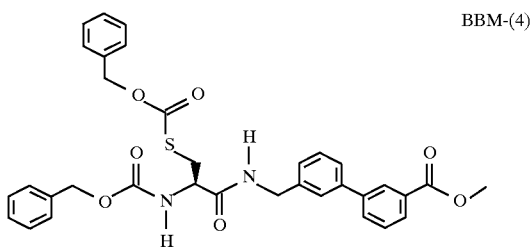

BBM-(4)

The functionalized derivatives of the phosphonates described earlier herein are also useful cell growth inhibitors. These derivatives may be illustrated by reference to compounds (5) and (6) as follows:

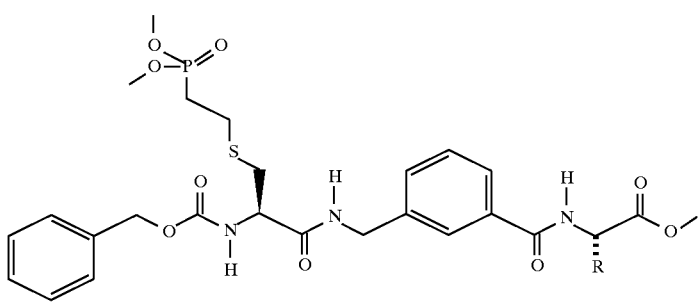

BMMM-(5)

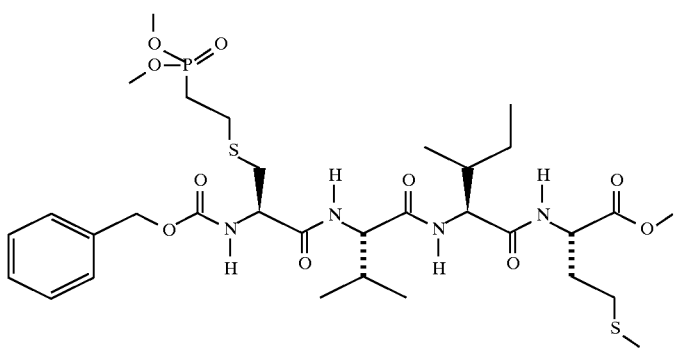

BMMM-(6)

In the above described BBM-compounds, the carboxylic group is esterified by methyl. The "BBM" used in the formulas represents a shorthand reference to the bis-(carboxybenzyloxy)methyl esters of C-AMBA-M, CVIM and compound (4). Correspondingly, the "BMMM" designation used with compounds (5) and (6) refers to the carboxy benzyloxy substitution and the three methyl groups in the methylated phosphoric and carboxylic acid end groups.

As noted, the purpose of the functional groups added to the parent compounds is to improve entry of the compounds into tumor cells. Once in the cells, the functional groups are removed to liberate the active compound to function in its inhibitory capacity.

As will be recognized by those in the art, the functionalized pro-drugs of the invention can be prepared using conventional and well-known procedures for esterifying amino, SH and carboxylic acid groups. Hence, details of such procedures are not essential for the preparation of the present pro-drugs. Other features of this aspect of the invention are, however, further described in the following examples.

EXAMPLE 11
Tumor Cell Growth Inhibitory Activity of Functionalized p21ras $CA_1A_2X$ Tetrapeptides and Pentidomimetics The ability of the peptides and their bis-carbobenzyloxy methyl ester derivatives (using BBM-$CA_1A_2X$; BBM-C-AMBA-M as examples) to inhibit tumor cell growth was determined by the well-known MTT assay. Ras oncogene-transformed EJ3 cells (a balbc 3T3 murine fibroblast (A-31) transformed with H-ras oncogene from a human bladder carcinoma) were exposed to various concentrations of peptides, peptidomimetics and their functionalized derivatives. Four days later, the percentage of live cells present relative to control was determined for each drug concentration. The extent of cell proliferation in the absence of drug was used as 100% proliferation.

Figure 4A:
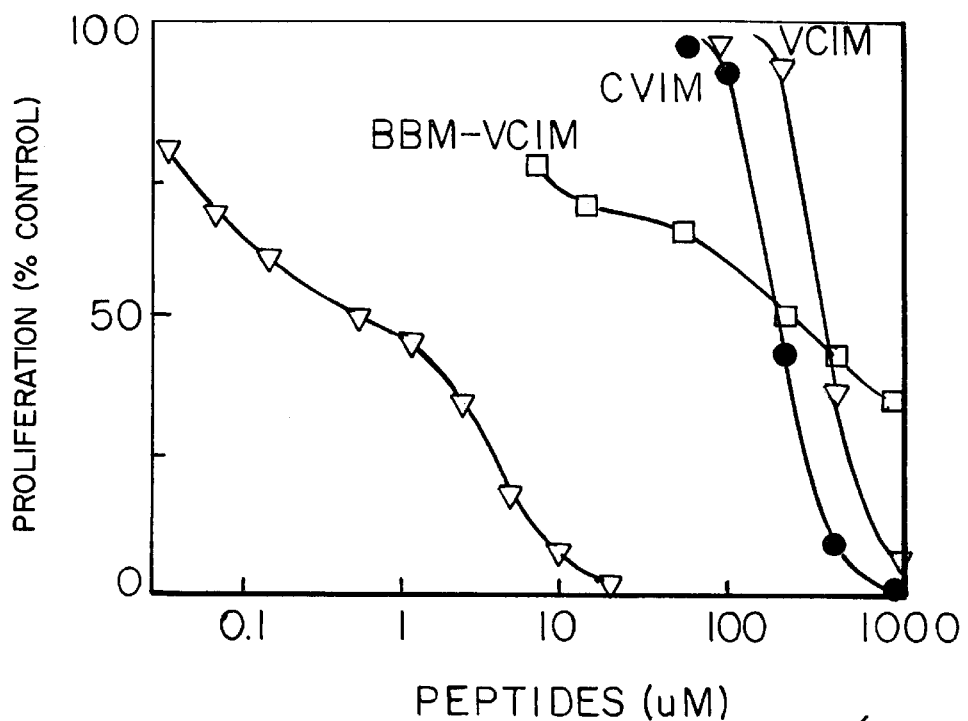
FIGS. 4A, 4B, 5A, 5B, 6, 7A and 7B illustrate further embodiments of the invention.

FIG. 4A shows that CVIM (a potent inhibitor of farnesyltransferase in vitro, $IC_{50}$=400 $\mu$M) inhibited EJ3 cell growth by 50% at an $IC_{50}$=250 gM whereas VCIM (a much weaker inhibitor of farnesyltransferase) ($IC_{50}$>10 $\mu$M) inhibited growth with $IC_{50}$ of 400 $\mu$M. BBM-CVIM was found to show a growth inhibitory $IC_{50}$ of only 0.7 $\mu$M while BBM-VCIM had an $IC_{50}$ of 200 $\mu$M. Thus, while both CVIM and VCIM were functionalized with the same lipophilic derivatives, the tumor growth inhibitory potency of CVIM increased by over 350-fold whereas that of VCIM increased by only 2-fold. The results also demonstrate that this remarkable increase in potency is not due to the functionalizing groups (carbobenzyloxy and methyl ester) since, while both CVIM and VCIM included these groups, only the potency of CVIM was greatly increased. Thus, the results clearly demonstrate that functionalization of only p21ras farnesyltransferase inhibitors increases their antitumor activity in vitro.

Figure 4B:
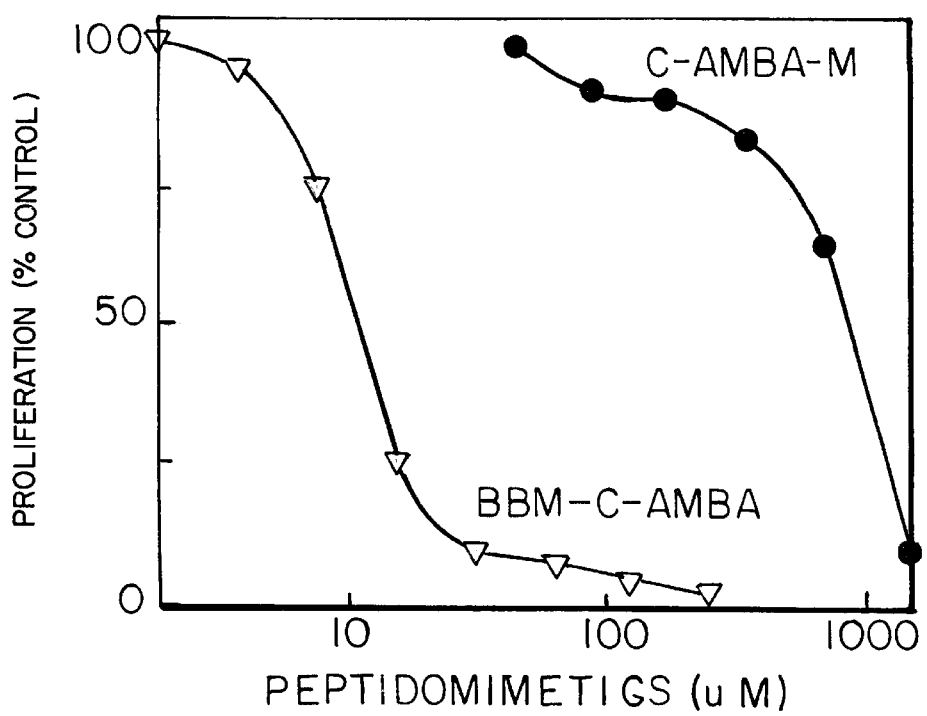

Similarly, the antitumor activity of BBM-C-AMBA-M in vitro was also much greater ($IC_{50}$=10 $\mu$M, FIG. 4B and Table 2) than its parent compound C-AMBA-M ($IC_{50}$=1500 $\mu$M). The discovery of these remarkable increases in the in vitro antitumor potencies of these novel compounds represents a very significant pharmacological finding.

EXAMPLE 12 p21ras Farnesyltransferase Inhibition

The ability of $CA_1A_2X$ tetrapeptides, peptidomimetics and corresponding functionalized derivatives to inhibit p21ras farnesyltransferase from EJ3 cells was determined in vitro as described above (Example 9). p21ras farnesyltransferase was partially purified from EJ3 cells by DEAE-chromatography as described above (Example 9) and incubated with various concentrations of peptides and peptidomimetics. The ability of these drugs to inhibit the transfer of [3H]FPP to recombinant p21ras was determined as described (Example 9).

Figure 5A:
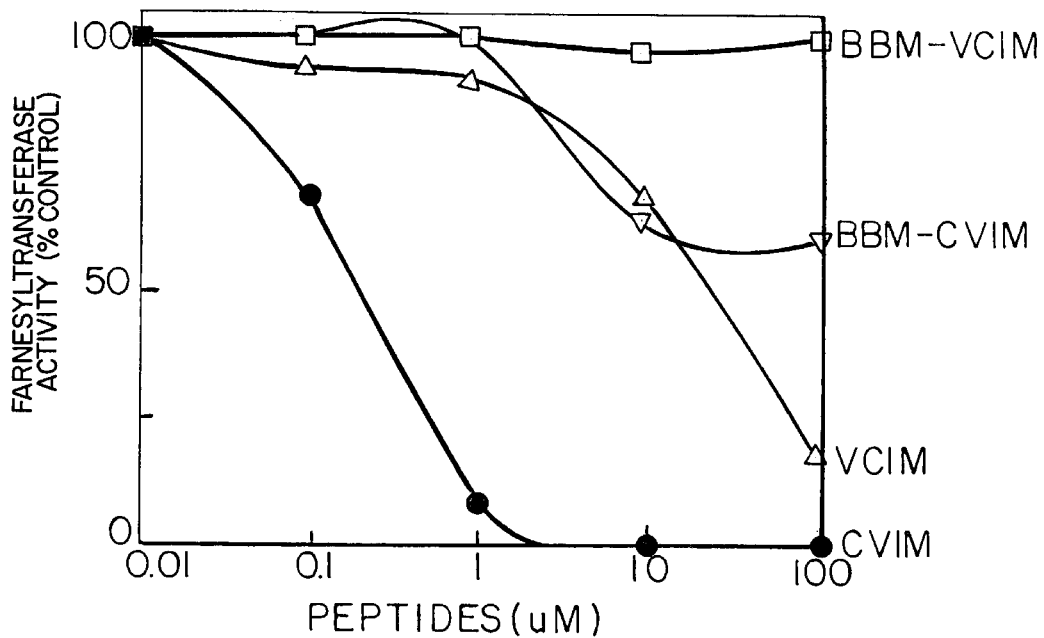
Figure 5B:
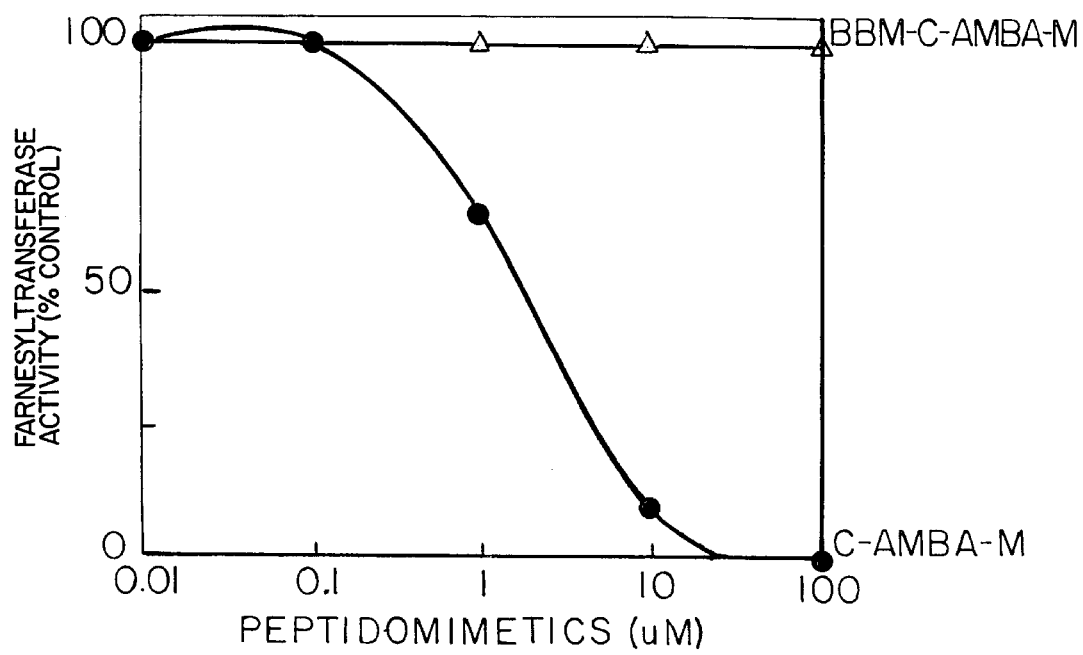

FIG. 5A shows that CVIM inhibited p21ras farnesyltransferase with an $IC_{50}$ of 400 nM whereas VCIM had an $IC_{50}$ of over 10 $\mu M$. Both BBM -CVIM and BBM-VCIM were ineffective in inhibiting the enzyme activity and had $IC_{50}$ of over 10 $\mu M$ (FIG. 5A and Table 2). Similar results were obtained with C-AMBA-M and BBM-C-AMBA-M where $IC_{50}$s were 2 $\mu M$ and over 100 $\mu M$, respectively (FIG. 5B and Table 2). These results demonstrate that functionalization of p21ras $CA_1A_2X$ peptides and peptidomimetics completely abolishes their ability to inhibit p21ras farnesyltransferase.

Figure 6:
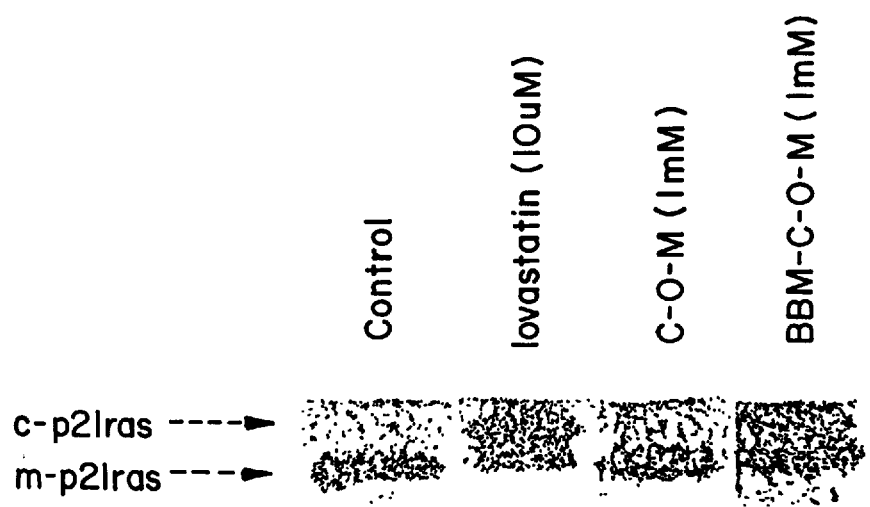

Viewed together, FIGS. 4A, 4B, 5A and 5B, and Table 2, show that only functionalized peptides and peptidomimetics are good tumor cell growth inhibitors and that only the non-functionalized peptides and peptidomimetics are good p21ras farnesyltransferase inhibitors. Coupled with the observation that only functionalized CVIM but not functionalized VCIM inhibit tumor cell growth potently, the results strongly demonstrate that functionalization of peptides and peptidomimetics increases their permeability to cellular plasma membranes which allows these agents to reach their critical target p21ras farnesyltransferase. The results indicate that the functionalized groups are removed in situ since only non-functionalized drugs are potent inhibitors of p21ras farnesyltransferase. This is indicated by FIG. 6. EJ3 cells were exposed to saline, lovastatin, C-AMBA-M or BBM-C-AMBA-M and p21ras immunoprecipitated with the anti-ras antibody Y13–259 (Oncogene Science Inc.). Membrane-bound and cytosolic p21ras were separated by SDS-PAGE and Western blotted with an anti-p21ras antibody (Y13–259). Control cells (saline-treated) contained only membrane-bound p21ras. Lovastatin which decreases the cellular pool of the farnesyltransferase substrate, FPP, inhibited p21ras membrane association as indicated by the appearance of the cytosolic p21ras band and the decrease in the levels of membrane-bound p21ras on the SDS-PAGE gel (FIG. 6). C-AMBA-M did not inhibit p21ras plasma association. This is consistent with the observation that C-AMBA-M is a weak inhibitor of tumor cell growth ($IC_{50}$=1500 $\mu M$, FIG. 4B, Table 2). In contrast, its functionalized derivative, BBM-C-AMBA-M, inhibited p21ras plasma membrane association (FIG. 6). These results demonstrate that functionalization of peptidomimetics with lipophilic, ester-containing groups allows them to be better taken up by cells so as to reach their critical target and consequently inhibit tumor cell growth with very high potency.

EXAMPLE 13

Tumor Growth Inhibitory Selectivity of Peptides and Peptidomimetics

Figure 7A:
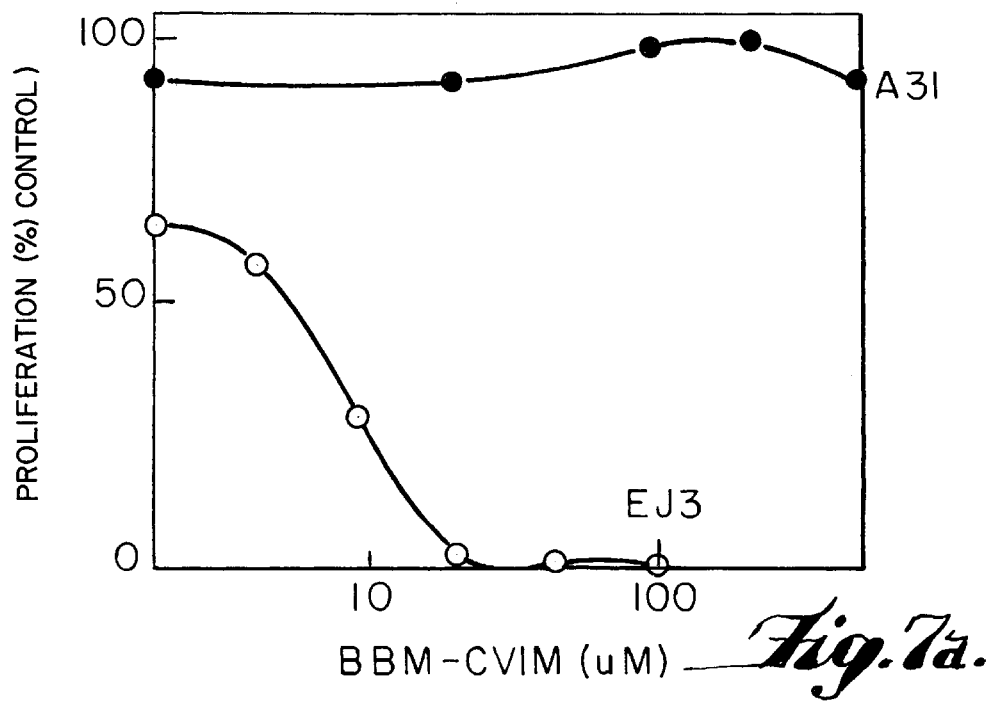
Figure 7B:
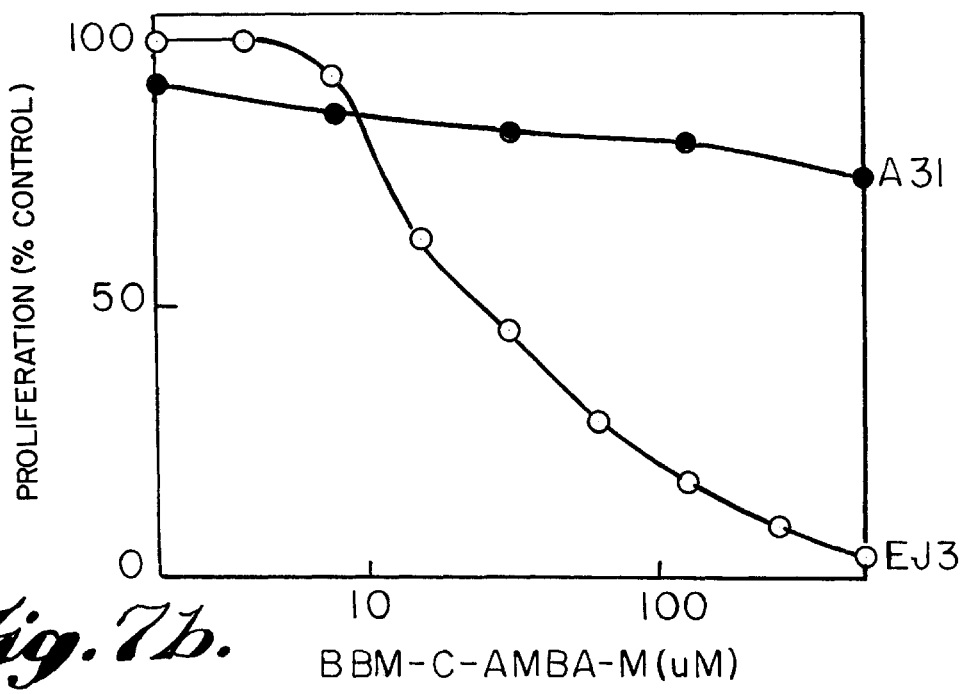

An important aspect of the invention is the finding that the antitumor activity of the peptidomimetics of the invention are selective for ras-transformed cells as compared to their non-transformed parent cell line. A-31 is a normal, non-tumorigenic cell line clone from balb murine fibroblasts. EJ3 is a tumorigenic (produces tumors when injected into mice) cell line that was obtained by transforming A-31 cells with H-ras isolated from a human bladder tumor. The ability of BBM-peptides and peptidomimetics to inhibit cell growth of these two related cell lines (A-31 and EJ3) was determined by MTT assay as described above. FIG. 7A shows that BBM-CVIM inhibited EJ3 cell growth with an IC50 of about 5 $\mu M$ whereas A-31 cell growth was inhibited with concentrations of 500 $\mu M$. Similarly, FIG. 7B shows that BBM-C-AMA-M inhibited EJ3 cells with an $IC_{50}$ of 20 $\mu M$ whereas A-31 cells growth was not much affected with concentrations of 500 $\mu M$.

Table 2 shows the $IC_{50}$ results in $\mu M$ for various compounds with respect to cell growth inhibition and p21ras farnesyltransferase inhibition.

TABLE 2

Inhibition of ras Oncogene-transformed cells

| COMPOUNDS | $IC_{50}$ (uM) Growth Studies | Farnesyltransferase |
|---|---|---|
| CVIM | 261 +/−57 | 0.350 |
| BBM-CVIM | 0.9 +/−0.4 | >100 |
| B-CVIM | 46 +/−8 | — |
| M-CVIM | 200 +/−58 | 4.5 |
| VCIM | 461 +/−68 | 40 |
| BBM-VCIM | 215 +/−66 | >100 |
| C-AMBA-M | 627 +/−178 | 3.1 |
| BBM-C-AMBA-M | 12.1 +/−1 | >100 |
| B-C-AMBA-M | 42 +/−18 | 6 |
| BB-Cys | 275 +/−41 | — |

In Table 2:
B-CVIM represents CVIM modified to include only a carboxybenzyloxy group on the terminal amino group
M-CVIM represents CVIM modified to include only methylated carboxy for the methionine carboxy group Literature references mentioned in the foregoing are more specifically identified as follows:

1. Barbacid, M., *Annu. Rev. Biochem.*, 56:779–828, (1987)
2. Grand, R. J. A. and Owen, D., *Biochem. J.*, 279:609–631, (1991)
3. Barbacid, M., *Important Advances in Oncology*, eds. Devita, Hellman & Rosenberg (Lippincott, Philadelphia, Pa.), pp. 3–22, (1986)
4. Mulcahy, L. S., Smith, M. R., and Stacey, D. W., *Nature*, 313:241–243, (1985)
5. Noda, M., Ko, M., Ogura, A., Liu, D. G>, Amano, T., Takano, T. and Ikawa, Y., *Nature*, 318:73–75, (1985)
6. Bar-Sagi, D. and Feramisco, J. R., *Cell*, 42:841–848, (1985)
7. Kataoka, T., Powers, S., McGill, C., Fasano, O., Strathern, J., Broach, J. and Wigler, M., *Cell*, 37:437–445, (1984)
8. Willumsen, B. M., Christensen, A., Hubbert, N. C., Papageorge, A. G. and Lowy, D. R., *Nature*, 310:583–586, (1984)
9. Willumsen, B. M., Norris, K., Papageorge, A. G., Hubbert, N. C. and Lowy, D. R., *EMBO J.*, 3:2581–2585, (1984)
10. Hancock, J. F., Magee, A. I., Childs, J. E. and Marshall, C. J., *Cell*, 57:1167–1177, (1989)
11. Gutierrez, L., Magee, A. I., Marshall, C. J. and Hancock, J. F., *EMBO J*, 8:1093–1098, (1989)
12. Casey, P. J., Solski, P. A., Der, C. J. and Buss, J. E., *Proc. Natl. Acad. Sci. USA*, 86:8323–8327, (1989)
13. Jackson, J. H., Cochrane, C. G., Bourne, J. R., Solski, P. A., Buss, J. E. and Der, C. J., *Proc. Natl. Acad. Sci. USA*, 87:3042–3046, (1990)
14. Hancock, J. F., Paterson, H. and Marshall, J. C., *Cell*, 63:133–139, (1990)

15. Reiss, Y., Goldstein, J. L., Seabra, M. C., Casey, P. J. and Brown, M. S., *Cell,* 62:81–88, (1990)
16. Reiss, Y., Seabra, M. C., Goldstein, J. L. and Brown, M. S., *METHODS: A Companion to Methods in Enzymology,* 1:241–245, (1990)
17. Reiss, Y., Seabra, M. C., Armstrong, S. A., Slaughter, C. A., Goldstein, J. L. and Brown, M. S., *J. Biol. Chem.,* 266:10672–10877, (1991)
18. Reiss, Y., Stradley, S. J., Gierasch, L. M., Brown, M. S. and Goldstein, J. L., *Proc. Natl. Acad. Sci. USA,* 88:732–736, (1991)
19. Manne, V., Roberts, D., Tobin, A., O'Rourke, E., DeVirgillio, M., Meyres, C., Ahmed, N., Kurz, E., Resh, M., Kung, H. F. and Barbacid, M., *Proc. Natl. Acad. Sci. USA,* 87:7541–7545, (1990)
20. Gibbs, J. B., *Cell,* 65:1–4, (1991)
21. Moores, S. L., Schaber, M. D., Mosser, S. D., Rands, E., O'Hara, M. B., Garsky, V. M., Marshall, M. S., Pompliano, D. L. and Gibbs, J. B., *J. Biol. Chem.,* 266:14603–14610, (1991)
22. Goldstein, J. L., Brown, M. S., Stradley, S. J., Reiss, Y. and Gierasch, L. M., *J. Biol. Chem.,* 266:15575–15578, (1991)
23. Brown, M. S., Goldstein, J. L., Paris, K. J., Burnier, J. P. and Marsters, J. C., *Proc. Natol. Acad. Sci. USA,* 89:8313–8316, (1992)
24. Pompliano, D. L., Rands, E., Schaber, M. D., Mosser, S. D., Neville, J. A. and Gibbs, J. B., *Biochemistry,* 31:3800–3807, (1992)
25. Lacal, J. D., Santos, E., Notario, V., Barbacid, M., Yamazaki, S., Kung, H. F., Seamans, O., McAndrew, S. and Crowl, R., *Proc. Natl. Acad. Sci. USA,* 81:5305–5309, (1984)
26. Stewart, F. H. C., *Aus. J. Chem.,* 36:2511, (1983)
27. Brown, M. J., Milano, P. D., Lever, D. C., Epstein, W. W. and Poulter, C. D., *J. Am. Chem. Soc.,* 113:3176, (1991)
28. Yang, C. C., Marlowe, C. K. and Kania, R., *J. Am. Chem. Soc.,* 113:3177, (1991)

It will be appreciated that various modifications may be made in the invention as described above without departing from the scope and intent of the invention as defined in the following claims wherein:

---

We claim:
1. A compound of the formula:

$\Delta_1 C \Delta$ $\Delta_1 CA_1A_2X$ or $\Delta_1 C\text{-}\beta\text{-}X$ where C is cysteine;

$A_1$, $A_2$ and X are peptide amino acids;

$\Delta$ is an aryl or heterocyclic substituent which does not include a peptide amino acid, and C and $\Delta$ are Joined through an amide linkage;

$\beta$ is a non-peptide aminoalkyl- or amino-substituted aliphatic or aromatic carboxylic acid or heteroaryl carboxylic acid or heterocyclic carboxylic acid; and $\Delta_1$ is an alkylphosphonic acid moiety bonded to the cysteine sulfhydryl group; or a pharmaceutically acceptable salt thereof.

2. A compound according to claim 1 of the formula:

$\Delta_1$ C-AMBA-X where $\Delta_1$, C and X have the meanings given in claim 1 and AMBA is an aminomethyl-benzoic acid.

3. A compound according to claim 2 wherein AMBA is 3-aminomethyl benzoic acid.

4. A method of inhibiting farnesyltransferase in a host where the farnesyltransferase is present which comprises administering to the host an effective amount of a compound according to one of claims 1–3.

5. A method for inhibiting tumor cell growth in a host which comprises administering to the host an effective amount of a compound according to one of claims 1–3.

* * * * *